United States Patent
Reilly et al.

(10) Patent No.: US 6,921,384 B2
(45) Date of Patent: Jul. 26, 2005

(54) FRONT LOADING INJECTOR WITH PRESSURE JACKET ASSEMBLY

(75) Inventors: David M. Reilly, Glenshaw, PA (US); Arthur E. Uber, III, Pittsburgh, PA (US); Alan D. Hirschman, Pittsburgh, PA (US); Eugene A. Gelblum, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 10/668,055

(22) Filed: Sep. 22, 2003

(65) Prior Publication Data

US 2004/0133152 A1 Jul. 8, 2004

Related U.S. Application Data

(60) Continuation of application No. 10/139,081, filed on May 3, 2002, now abandoned, which is a division of application No. 10/121,934, filed on Apr. 12, 2002, now abandoned, which is a continuation of application No. 09/304,934, filed on May 4, 1999, now Pat. No. 6,371,938, which is a continuation of application No. 08/911,338, filed on Aug. 14, 1997, now Pat. No. 5,899,885, which is a division of application No. 08/519,201, filed on Aug. 25, 1995, now Pat. No. 5,779,675.

(51) Int. Cl.[7] ............................................. A61M 37/00
(52) U.S. Cl. ........................ 604/131; 604/154; 604/151; 128/DIG. 1
(58) Field of Search ................................. 604/131, 134, 604/140, 143, 151, 152, 154, 218, 227, 228, 232, 233, 155; 600/432; 128/DIG. 1, 655; 222/390, 391, 327

(56) References Cited

U.S. PATENT DOCUMENTS

| | | | |
|---|---|---|---|
| 1,157,552 A | 10/1915 | Kispert | |
| 1,667,273 A | 4/1928 | Stewart | |
| 1,704,921 A | 3/1929 | Nicoll | |
| 1,718,603 A | 6/1929 | Smith | |
| 1,747,243 A | 2/1930 | Hoskins | |
| 1,819,258 A | 8/1931 | Nevin | |
| 2,475,061 A | 7/1949 | Smith | |
| 2,602,571 A | 7/1952 | Sherbondy | |
| 2,627,270 A | 2/1953 | Glass | |
| 2,634,889 A | 4/1953 | Sherbondy | |

(Continued)

FOREIGN PATENT DOCUMENTS

| | | | |
|---|---|---|---|
| DE | 34 43 435 | * | 6/1986 |
| EP | 0 092 607 | * | 11/1983 |
| EP | 0 279 922 | * | 8/1988 |
| WO | WO 97/07841 | * | 3/1997 |

OTHER PUBLICATIONS

International Search Report for Counterpart PCT Application PCT/US96/13324.

*Primary Examiner*—Sharon Kennedy
(74) *Attorney, Agent, or Firm*—Gregory L. Bradley; Henry E. Bartony, Jr.

(57) ABSTRACT

An injection apparatus for use with a syringe is provided. The injection apparatus includes an injector and a pressure jacket assembly. The injector preferably includes a housing defining a front opening and a drive piston extendible through the front opening for imparting motive force to a plunger disposed within the syringe. The pressure jacket assembly preferably includes a jacket cylinder having a rear end coupled to the injector housing and an open front end for receiving the syringe therethrough, a support member having a rear end pivotally coupled to the injector housing and a front end, and a front member pivotally coupled to the front end of the support member. Preferably, the front member is pivotable between a closed position for retaining the syringe within the jacket cylinder and an open position for allowing the syringe to be inserted into and removed from the front end of the jacket cylinder.

9 Claims, 12 Drawing Sheets

U.S. PATENT DOCUMENTS

| | | |
|---|---|---|
| 2,702,547 A | 2/1955 | Glass |
| 3,395,704 A | 8/1968 | Frey et al. |
| 3,623,474 A | 11/1971 | Heilman |
| 3,880,138 A | 4/1975 | Wootten et al. |
| 3,964,139 A | 6/1976 | Kleinmann et al. |
| 3,997,085 A | 12/1976 | Lindquist |
| 4,065,034 A | 12/1977 | Callan |
| 4,351,335 A | 9/1982 | Whitney et al. |
| 4,424,720 A | 1/1984 | Bucchianeri |
| 4,493,704 A | 1/1985 | Beard et al. |
| 4,677,980 A | 7/1987 | Reilly et al. |
| 4,695,271 A | 9/1987 | Goethel |
| 4,723,948 A | 2/1988 | Clark et al. |
| 5,078,698 A | 1/1992 | Stiehl et al. |
| 5,219,099 A | 6/1993 | Spence et al. |
| 5,228,883 A | 7/1993 | Blakely et al. |
| 5,300,031 A | 4/1994 | Neer et al. |
| 5,336,189 A | 8/1994 | Sealfon |
| 5,383,858 A | 1/1995 | Reilly et al. |
| 5,400,925 A | 3/1995 | Simmen |
| 5,520,658 A | 5/1996 | Holm |
| 5,535,746 A | 7/1996 | Hoover et al. |
| 5,779,675 A | 7/1998 | Reilly et al. |
| 5,882,343 A | 3/1999 | Wilson et al. |
| 5,899,885 A | 5/1999 | Reilly et al. |
| 5,938,639 A | 8/1999 | Reilly et al. |
| 6,241,708 B1 | 6/2001 | Reilly et al. |
| RE37,487 E | 12/2001 | Reilly et al. |
| 6,371,938 B1 | 4/2002 | Reilly et al. |
| 2002/0128601 A1 | 9/2002 | Reilly et al. |
| 2004/0024359 A1 | 2/2004 | Reilly et al. |

\* cited by examiner

FRONT LOADING INJECTOR WITH PRESSURE JACKET ASSEMBLY

CROSS-REFERENCE TO RELATED APPLICATIONS

This application is a continuation of application Ser. No. 10/139,081, filed on May 3, 2002, now abandoned, which is a division of application Ser. No. 10/121,934, filed on Apr. 12, 2002, now abandoned, which is a continuation of application Ser. No. 09/304,934, filed on May 4, 1999, now U.S. Pat. No. 6,371,938, which is a continuation of application Ser. No. 08/911,338, filed on Aug. 14, 1997, now U.S. Pat. No. 5,899,885, which is a division of application Ser. No. 08/519,201, filed on Aug. 25, 1995, now U.S. Pat. No. 5,779,675, the contents of which are incorporated herein by reference.

BACKGROUND OF INVENTION

This invention relates to pressure jacket systems for securing a syringe in an injector head. More specifically, the invention relates to pressure jacket systems which allow front loading and removal of a syringe, and which hold the syringe securely to an injector head during injection procedures.

In the medical field, patients often are injected with fluids in procedures such as angiography. In such procedures, which require controlled injection of a large volume of fluid into a patient, a needle is used as a conduit for the fluid which is connected to the syringe by a connector tube. The syringe is mounted on a motorized injector having an injector head.

For long term compatibility with injectable fluids, syringes may be made of polypropylene with a certain minimum wall thickness. The thickness is critical as typical pressures of up to 1200 p.s.i. are used to inject the fluids into a patient. For safety and sanitary reasons, different disposable syringes are used or different fluids and different patients.

Pressure jackets are known in the art for enclosing and retaining syringes while in use. A pressure jacket serves to limit radial expansion of a syringe which may lead to bursting or to leaks of the pressurized fluid around the seals of the syringe plunger. Another function of a pressure jacket is to prevent forward motion of the syringe. For example, typically a force of 2000 pounds is required to restrain the forward motion of a 200 ml syringe with a cross-section of 1.7 in.$^2$ at 1200 p.s.i.

Certain present pressure jackets are one piece designs, where the syringe is inserted into the jacket from the rear end of the jacket. An example of such a pressure jacket is found in U.S. Pat. No. 4,677,980, assigned to the common assignee of this application. The neck of the syringe protrudes from the front end of the pressure jacket for connection of fluid lines that lead to the patient. Because the diameter of the syringe neck is much smaller than that of the syringe barrel, it can withstand both radial and forward force.

However such an arrangement causes a problem when the syringe is removed from the pressure jacket. The neck of the syringe must pass through the present pressure jacket configurations. This requires the patient fluid path to be disconnected, which presents a potential biohazard and may result in spilling fluids onto the pressure jacket. Additionally, fluid spilled during loading and purging air from the syringe may get inside the pressure jacket and require cleaning.

Thus, a pressure jacket system is needed which permits a syringe to be front loaded onto an injector head and removed from the injector head without disconnecting the patient fluid path. Further, a pressure jacket system is needed which reduces the materials required for the manufacture of the syringe.

SUMMARY OF INVENTION

The present invention relates to front loadable pressure jacket systems for use with injectors having an injector head with a housing and a front opening. A syringe is connected to the injector front opening to allow the flow of fluids through the syringe. A pressure jacket holds the syringe to the injector head. A piston extendible through the injector front opening imparts motive force to a plunger in the syringe to cause fluid flow.

One embodiment of the present invention is a pressure jacket having first and second jacket halves each having interior surfaces conformable to the exterior surface of the syringe. A hinge pin extends from the front face of the injector head. The first and second jacket halves are rotatably mounted on the hinge pin. The halves may be placed in an open position allowing insertion and removal of the syringe or a closed position so that the jacket surrounds the syringe.

A second embodiment of the present invention includes a pressure jacket with first and second jacket halves, where each jacket half has a front or distal end and a rear or proximal end. A hinge for rotational connection to the injector's front face allows the first and second jacket halves to be placed in an open position, allowing insertion and removal of the syringe, and a closed position such that the jacket substantially surrounds the syringe. A locking ring is disposed around the first and second jacket halves. The locking ring is placed in a position over the front ends of the first and second jacket halves when in the closed position and the ring is placed in a position near the proximal ends of the jacket halves when in the open position.

A third embodiment of the present invention includes a pressure jacket that has a hollow cylinder portion with an open distal end and a rear end coupled to the injector head. The cylinder has at least one locking finger having front and rear ends, and a pivot axis disposed near the rear end. The pivot axis is connected to the open distal end of the cylinder. The locking finger is pivotable to a closed position such that the front end of the finger acts to hold the syringe within the cylinder. The finger is pivotable to an open position to allow the insertion or removal of the syringe.

A fourth embodiment of the present invention includes a pressure jacket having a jacket cylinder with an open front end and a rear end coupled to the injector head. A first tie rod has a rear end attached to the injector head and a front end that is attached to a first front plate. The first front plate is pivotable between a closed position for holding the syringe within the jacket cylinder and an open position for allowing the insertion or removal of the syringe. A second tie rod likewise has a rear end attached to the injector head and a front end attached to a second front plate. The second front plate is pivotable between a closed position for holding the syringe within the jacket cylinder, and an open position for allowing the insertion or removal of the syringe.

A fifth embodiment of the present invention includes a pressure jacket with a jacket cylinder having an open front end and a rear end coupled to the injector head. A first pivot is coupled to the injector head and a first tie rod is attached to the first pivot. A second pivot is coupled to the injector head and a second tie rod is attached to the second pivot. A front retaining plate joining the front ends of the tie rods allows the retaining plate to be pivotable between a closed position for holding the syringe within the jacket cylinder and an open position to allow the insertion or removal of the syringe from the jacket cylinder.

A sixth embodiment of the present invention includes a pressure jacket which has a jacket cylinder formed around a longitudinal axis and having an open front end and a rear end. The jacket cylinder is transversely pivoted to the front face of the housing to allow the cylinder jacket to be pivoted between a closed position and an open position. An arm having a rear end affixed to the injector head is attached to a retaining member. The retaining member retains the syringe in the jacket cylinder when the jacket cylinder is in a closed position. The jacket permits the loading or removal of the syringe when the jacket cylinder is in an open position.

A seventh embodiment of the present invention includes a pressure jacket that has a slidable canopy retractable within the injector head. An arm having a rear end is coupled to the injector head. The front end of the arm is coupled to a retaining member and retains the syringe. The canopy slides to a closed position to retain the syringe and slides to an open position to allow the insertion or removal of the syringe.

DETAILED DESCRIPTION OF THE INVENTION

Figure 1:
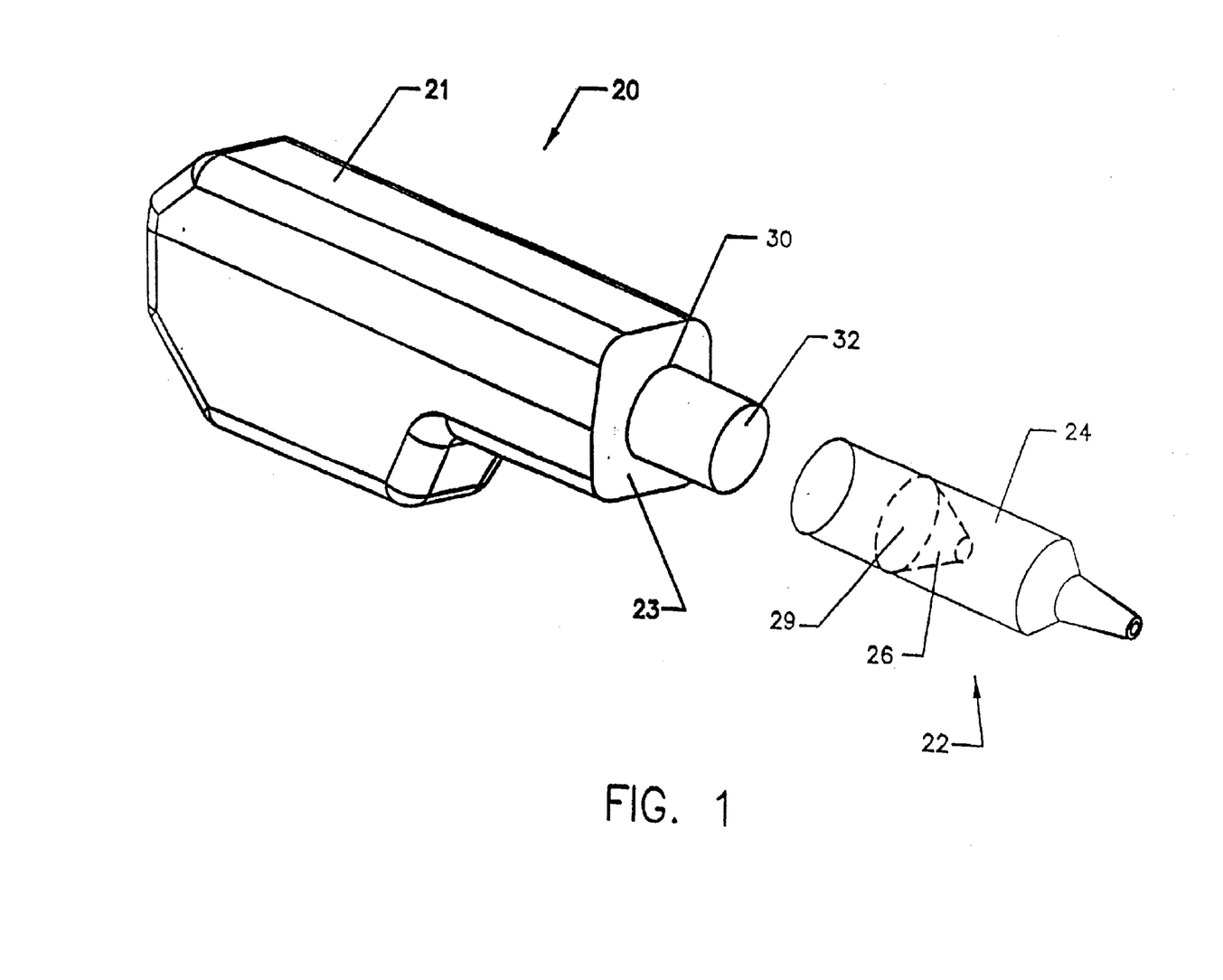
FIG. 1 is a schematic view of an injector head and front loading syringe that may be used with the embodiments of the present invention.

FIG. 1 shows an injector head indicated generally at 20 and a syringe 22 which may be used in connection with various embodiments of the present invention. The injector head 20 includes a housing 21 and a front face 23. The injector head 20 is used to actuate syringe 22, which is mounted on the injector head 20. The syringe 22 includes a tubular body 24 and a plunger 26 slidably positioned therein. In operation, the rear of the syringe 22 is fixed in or against an opening 30 on the injector front face 23. Syringe 22 may be affixed to opening 30 by any suitable means, such as mounting flanges (not shown), as described in U.S. Pat. No. 5,383,858, assigned to the common assignee of this application and which is fully incorporated herein by reference. Any of the pressure jacket systems described below may be used to retain syringe 22 when syringe 22 is affixed to the injector front face 23. The fluid within syringe 22 is pushed forward by a drive means, such as motorized piston 32, extendable and retractable through opening 30, which engages the rear surface 29 of plunger 26 to push plunger 26 forward in the syringe.

Figures 2, 3:
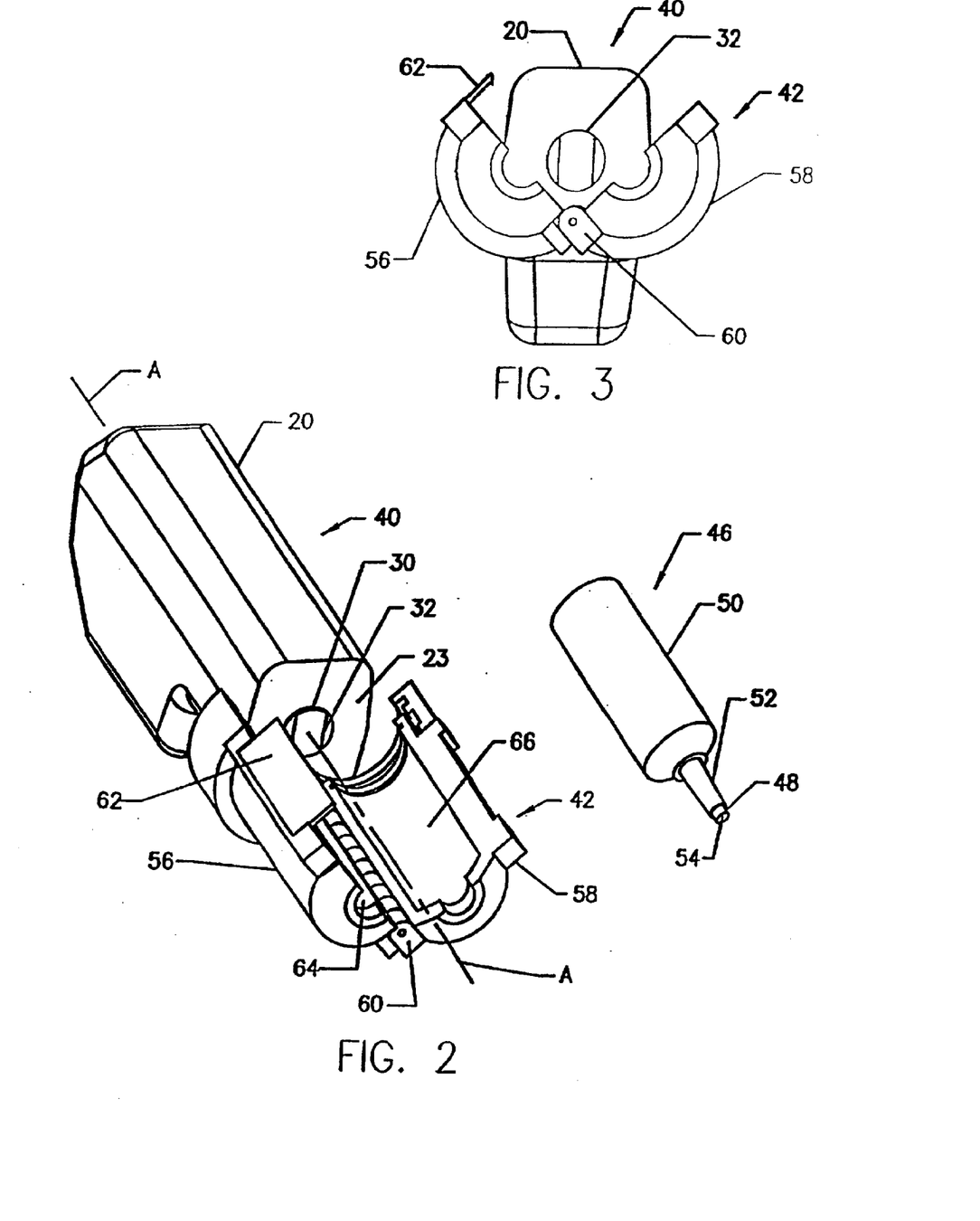
FIG. 2 is a perspective view of a first embodiment of the invention in an open position.
FIG. 3 is a front elevational view of the first embodiment of the invention in an open position.
Figures 4, 5:
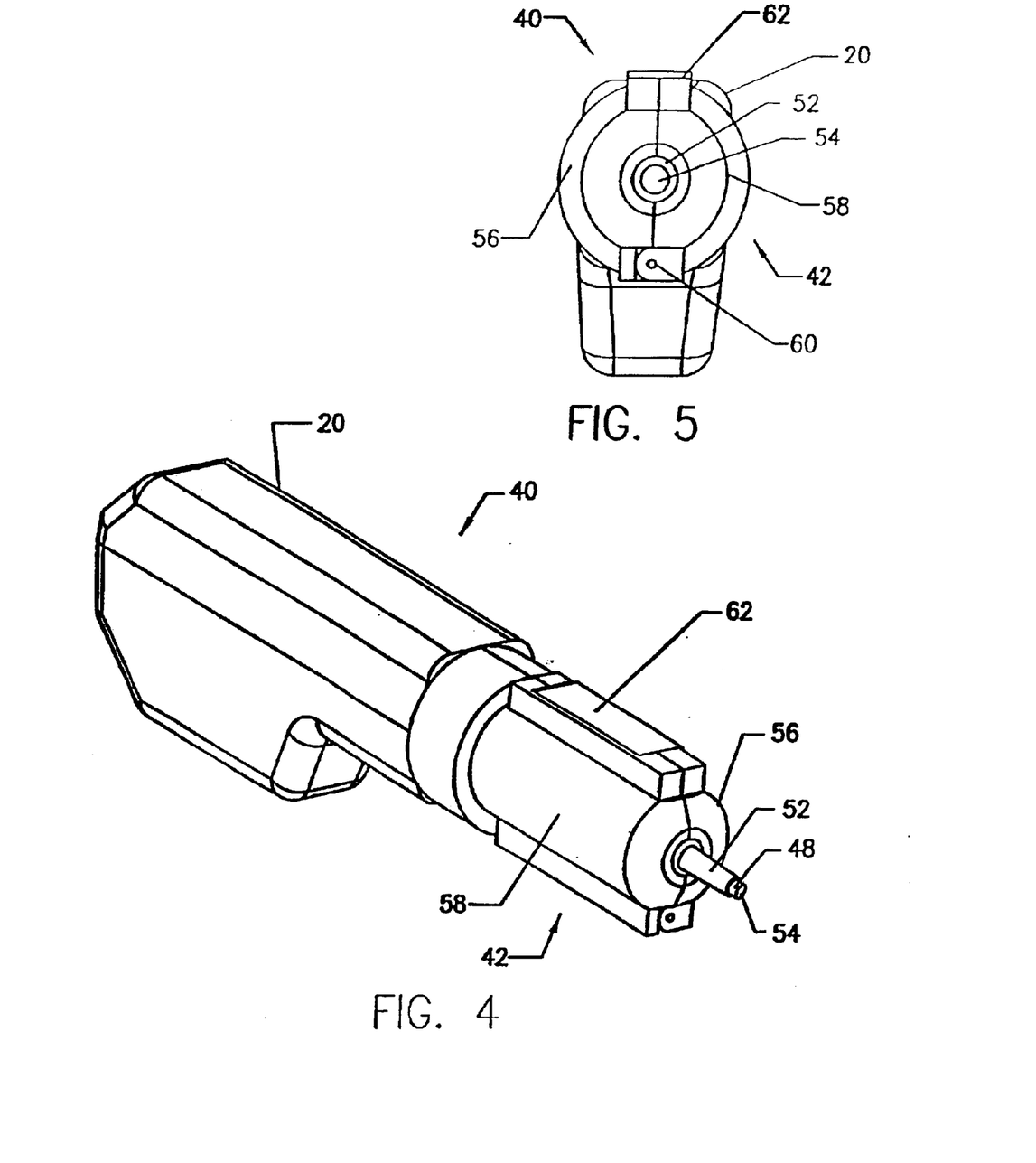
FIG. 4 is a perspective view of the first embodiment of the present invention in a closed position.
FIG. 5 is a front elevational view of the first embodiment of the present invention in a closed position.

FIGS. 2–3 show views of a first embodiment of the present invention in an open position and FIGS. 4–5 show views of the first embodiment in a closed position. Specifically, as shown in detail in FIG. 2, a fluid injector 40 includes a pressure jacket 42 which is of an axially split or "clam shell" type. The pressure jacket 42 is mounted to the front face 23 of the injector head 20. When syringe 46 is installed into pressure jacket 42, as more fully described below, motorized piston 32 when driven forward, engages a syringe plunger (not shown) and pushes the plunger forward in the body of a syringe 46 to force fluid out of the syringe tip 48. Syringe 46, preferably manufactured of a clear plastic, includes a body 50, a neck 52 connected to the body 50 and a luer connector 54 connected to the neck 52. A connector tube (not shown) may be connected to luer connector 54, which delivers fluid to the patient.

As shown in FIGS. 2–3, pressure jacket 42 which includes a first jacket half 56 and a second jacket half 58, is preferably manufactured from a clear plastic so that the position of the plunger within installed syringe 46 may be observed. The first jacket half 56 and the second jacket half 58 have interior surfaces, 64 and 66, respectively, which conform to the exterior surface of the body 50 of the syringe 46. The first and second jacket halves 56 and 58 are joined by a pivot hinge 60 which allows the first jacket half 56 and the second jacket half 58 to be swung to an open position, as shown in FIGS. 2 and 3. Pivot hinge 60 has one end thereof affixed to the forward wall of injector head 20 at a point below injector head opening 30, although in other embodiments the pivot hinge 60 may otherwise be radially displaced from opening 30. For example, if it were desired that jacket halves 56 and 58 open to the side instead of from the top, the pivot hinge 60 would be positioned to one side of opening 30. As shown in FIG. 2, the pivot hinge 60 is preferably parallel to axis A of the injector piston movement. With the pressure jacket 42 in the open position, syringe 46 may be inserted between the first jacket half 56 and the second jacket half 58. The two jacket halves 56 and 58 are then closed and locked by means of a latch 62, as shown in FIGS. 4 and 5, which in the illustrated embodiment is attached to first jacket half 56. Alternatively, one of the first or second jacket halves 56 or 58 may be fixed to the forward wall 23 of injector head 20 and the other jacket half may be pivotally mounted to the forward wall 23 of injector head 20.

As shown in FIGS. 2–5, the first embodiment of the present invention allows front loading and removal of syringe 46 and any tubes attached thereto while minimizing fluid spills. Further, as syringe 46 is retained within pressure jacket 42, the amount of material required to manufacture syringe 42 is reduced because the pressure jacket 42, instead of the syringe walls, bears the majority of the pressure force exerted during a fluid injection procedure.

Figure 6:
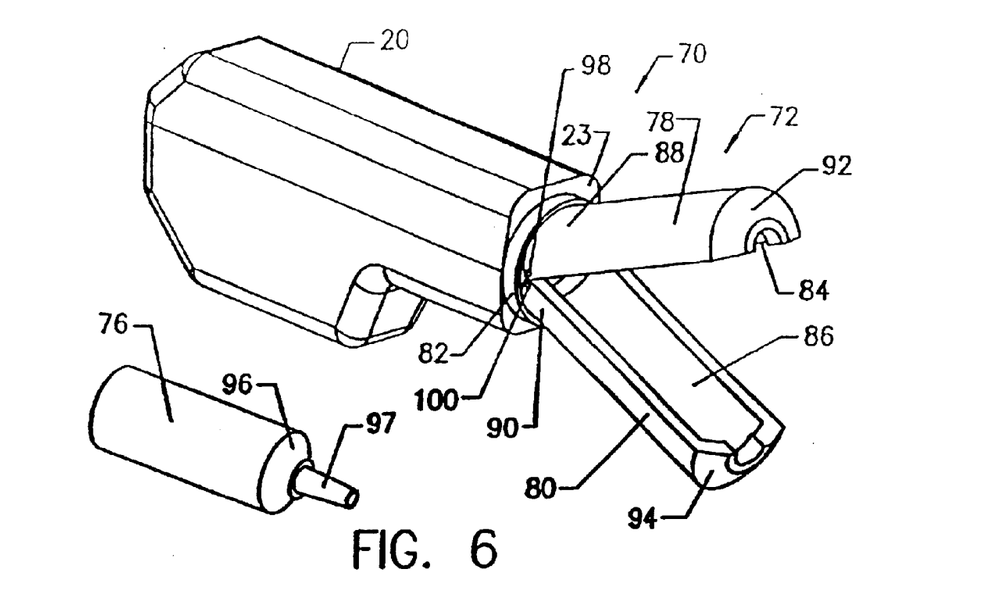
FIG. 6 is a perspective view of a second embodiment of the present invention in an open position.
Figure 7:
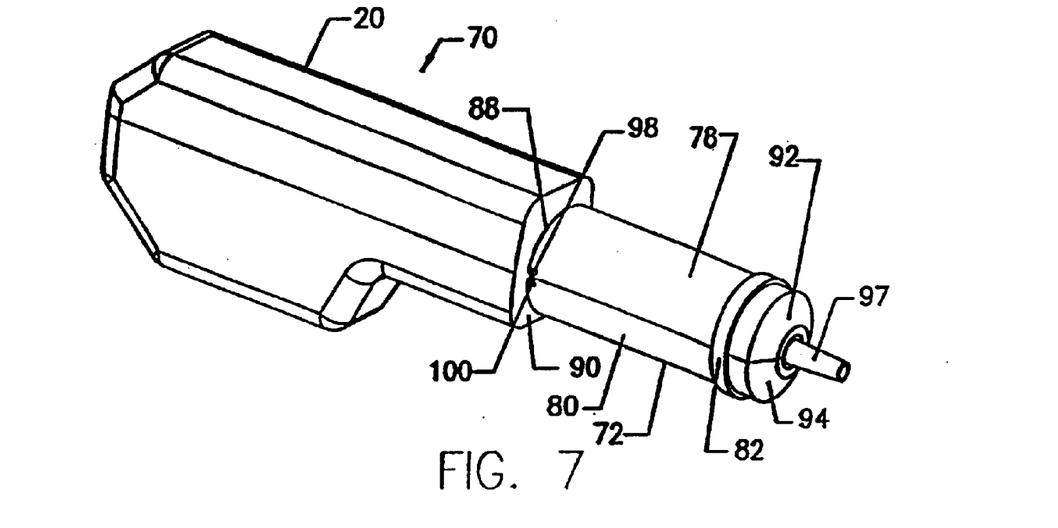
FIG. 7 is a perspective view of the second embodiment of the present invention in a closed position.

A second embodiment of the present invention is shown in FIGS. 6 and 7. FIG. 6 shows a fluid injector 70 having a pressure jacket system 72 in an open position, which permits the loading and removal of a syringe 76. Pressure jacket 72, a generally "alligator jaw" type, is hingedly affixed to an injector head 20 to which syringe 76 may be releasably installed. Specifically, as shown in FIG. 7, syringe 76 is held by a combination of a first or top jacket half 78 and a second or bottom jacket half 80, together forming pressure jacket 72, and a locking ring 82. Both top jacket half 78 and bottom jacket half 80 are preferably made of clear plastic and have a semi-cylindrical shape. Interior semi-cylindrical surfaces 84 and 86 of top and bottom jacket halves 78 and 80, respectively, conform to the exterior surface of the body of the syringe 76. Jacket halves 78 and 80 have respective rear ends 88 and 90 located near the injector front face 23 and front ends 92 and 94 which coact to form an opening for the syringe neck 97. The front ends 92 and 94 have interior surfaces that mate with the exterior conical transition region 96 of syringe 76.

When the top jacket half 78 and bottom jacket half 80 are in the closed position, as shown in FIG. 7, the locking ring 82 is placed about jacket halves 78 and 80, preferably near the front ends 92 and 94 of jacket halves 78 and 80. The top jacket half 78 is rotatable around a first hinge pin 98 while the bottom jacket half 80 is rotatable around a bottom hinge pin 100. In order to open the pressure jacket 72, the locking ring 82 is moved along the length of the top jacket half 78 and bottom jacket half 80 to the injector front face 23, as shown in FIG. 6. This allows the pressure jacket 72 to be opened by moving the top jacket half 78 about the first hinge pin 98 and moving the bottom jacket half 80 about the second hinge 100. A link (not shown) between the two jacket halves 78 and 80 may be used to regulate the movement of the two halves so they move away and toward each other at the same rate. Alternatively, either the top or bottom jacket halves 78 or 80 may be fixed to the injector front face 23 while the other jacket half is pivotally mounted to the injector front face 23. While in the open position, the syringe 76 may be inserted or removed from the pressure jacket 72. The advantages relating to the first embodiment of the present invention, discussed above, are also realized with this second embodiment.

FIGS. 8–11 show a third embodiment of the present invention. A fluid injector indicated generally at 110 includes a pressure jacket 112 with a plurality of locking fingers 114 for engaging a syringe 116, shown in an open position in FIG. 10 and a closed position in FIG. 11. Pressure jacket 112 is connected at its rear end 132 to injector head 20 by any suitable means, such as a threaded connection (not shown). Syringe 116 has a cylindrical body 118 having a front end 120 and an open rear end 122. The front end 120 of syringe 116 is tapered and connected to a neck 124. A disk shaped drip flange 126 is formed around the neck 124.

Figure 10:
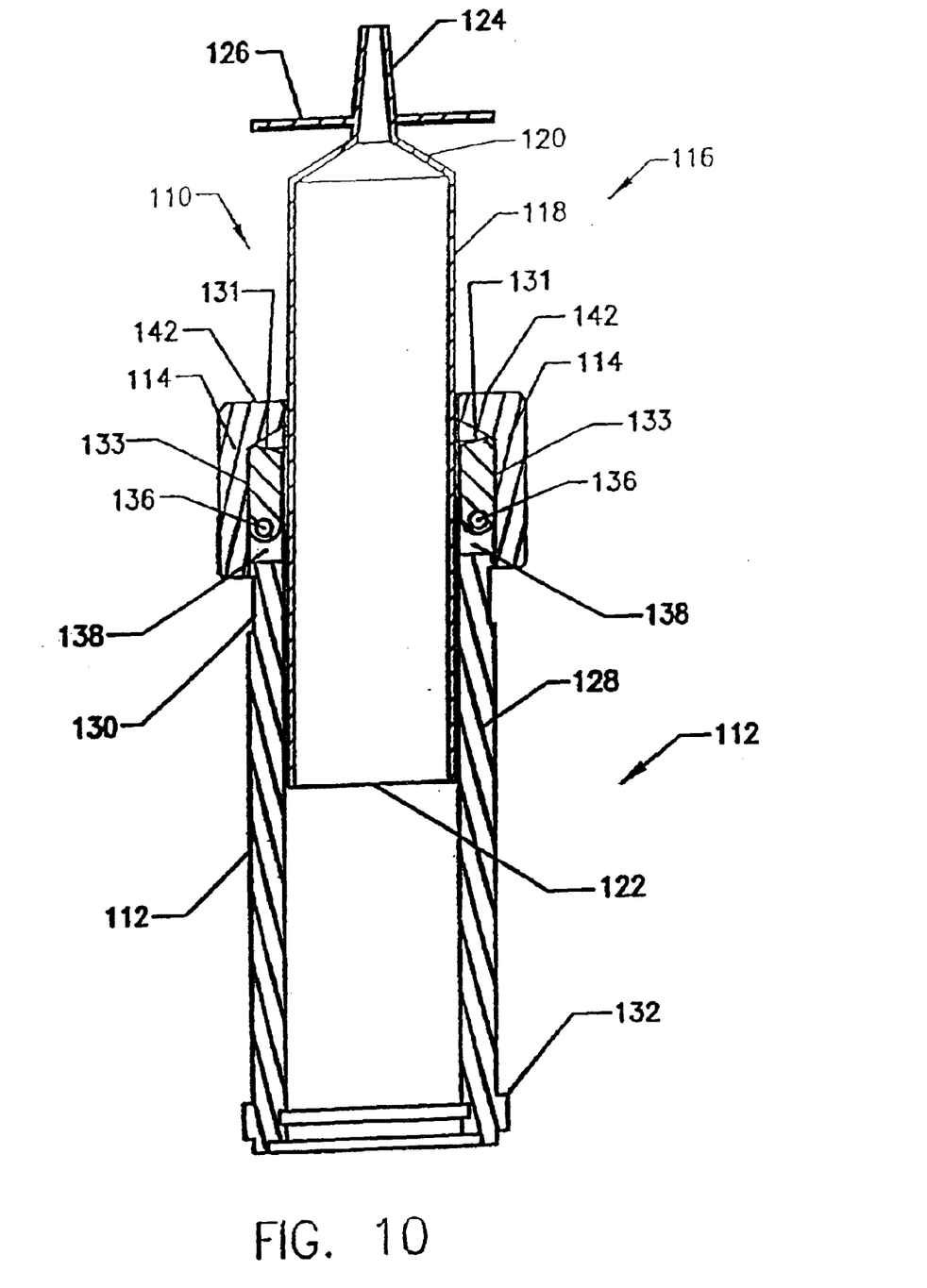
FIG. 10 is a front elevational view of a third embodiment of the present invention in an open position.

The pressure jacket 112 includes a hollow cylinder 128 that is preferably made of clear plastic. A distal end 130 of the cylinder 128 is open to allow loading and removal of the syringe 116. The distal end 130 of pressure jacket 112 has an outside surface 134 that is slightly smaller in diameter than that of cylinder 128. The outside surface 134 of the distal end 130 is threaded (not shown). A plurality of locking fingers 114 (in the illustrative embodiment, six are shown) pivot about respective pivot points 136, as shown in FIG. 10. Each locking finger 114 has a front end 131, preferably beveled, and a rear end 133. Pivot points 136 are located proximate to the rear ends 133 of the locking fingers 114 and are mounted within channels 138 located on the rim of distal end 130. Locking fingers 114 may be kept in position by means of friction and are radially angularly spaced from each other on the rim of distal end 130. It is understood that any number of locking fingers may be used.

Figure 8:
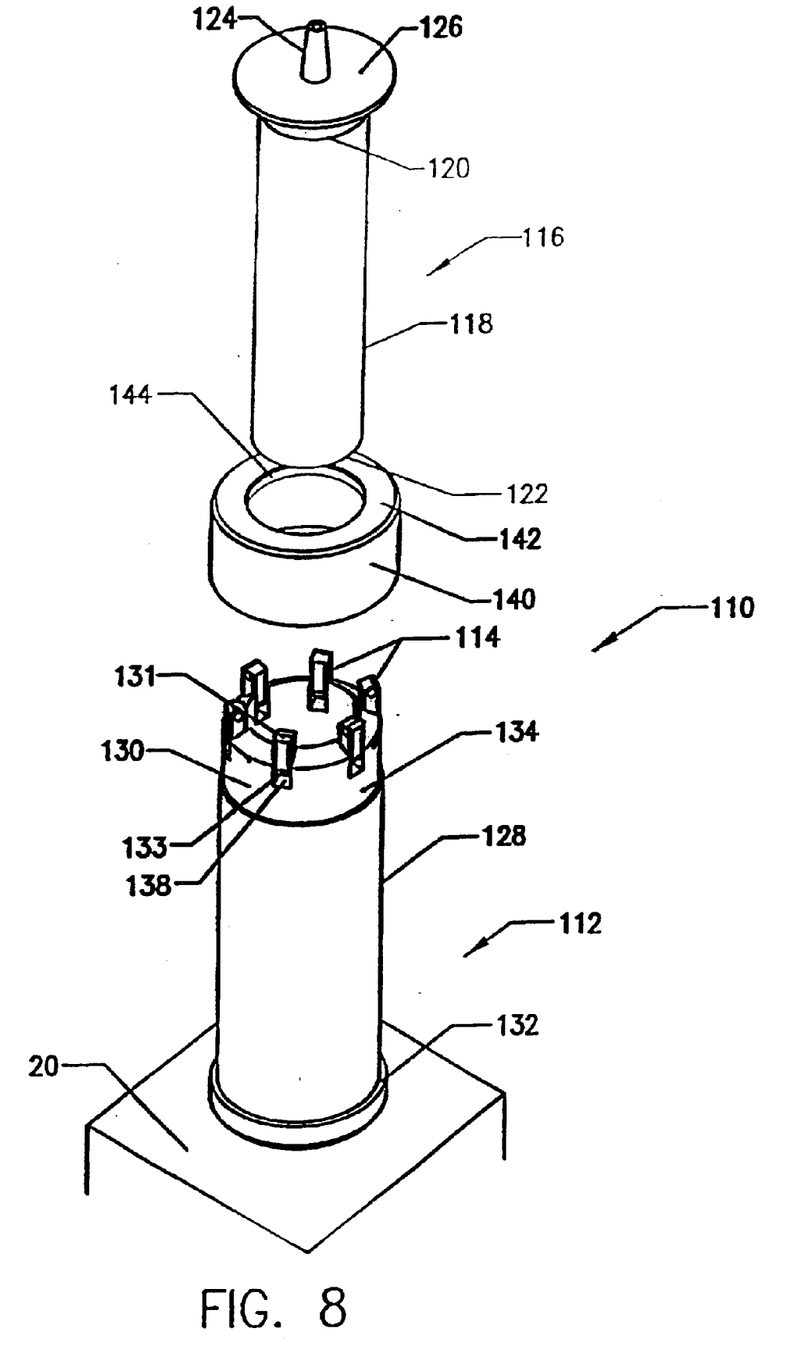
FIG. 8 is an exploded view of a third embodiment of the present invention.
Figure 11:
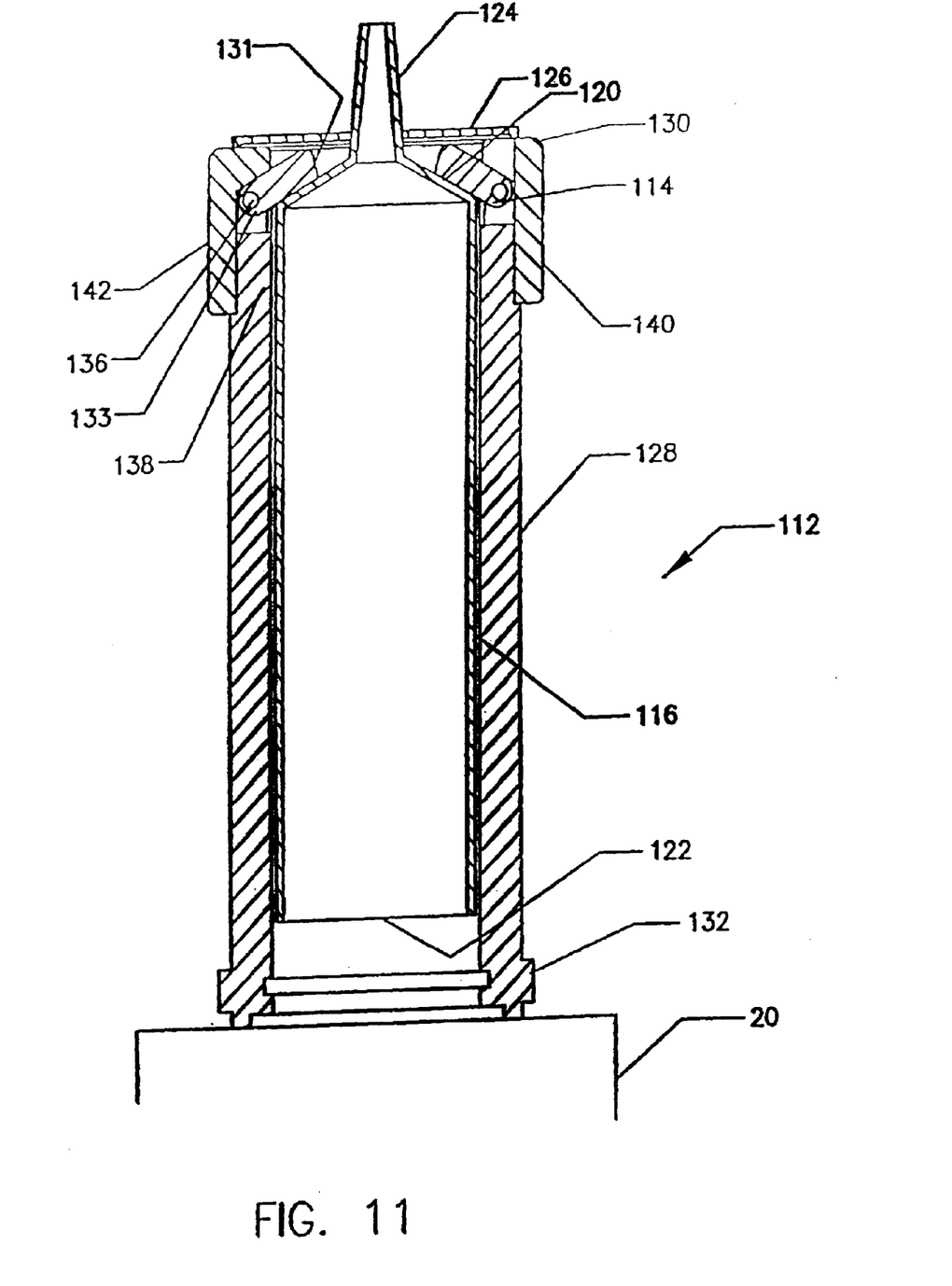
FIG. 11 is a front elevational view of the third embodiment of the present invention in a closed position.

As shown in FIGS. 8, 10 and 11, a locking ring 140, generally cylindrical in shape, is threaded on its interior surface and threaded onto the outside surface 134 of the distal end 130 (threads not shown). The front end 142 of the locking ring 140 is a distal annulus extending radially inwardly to form an open orifice 144 which permits the syringe body 118 to be inserted into pressure jacket 112, but does not permit the drip flange 126 to be inserted into pressure jacket 112. FIG. 10 shows that the front interior surface of the front end 142 is sloped to engage locking fingers 114 when in a closed position, as shown in FIG. 11 and more fully described below.

FIGS. 10 and 11 show that the syringe 116 is inserted into locking ring 140 and cylinder 128 so that drip flange 126 rests on the front end 142. Locking ring 140 is screwed further onto cylinder 128, and thus, moved toward the rear end 132 of cylinder 128, as shown in FIG. 11. Locking fingers 114 are pivoted about there respective pivot points 136 from the open position of FIG. 10 to the closed position of FIG. 11 by the sloped interior surface of the locking ring 142 which engages the distal ends 133 of the locking fingers 114. Front ends 131 of fingers 114 retain syringe 116 in place. When locking ring 140 is unscrewed away from the distal end 130 of the cylinder 128, locking fingers 114 pivot into an open position. A spring member (not shown) may be used to bias the locking fingers 114 into the open position. Syringe 116 may then be removed from or inserted into the pressure jacket 112. The advantages relating to the first embodiment, as discussed above, are also realized by this embodiment.

Figure 9A:
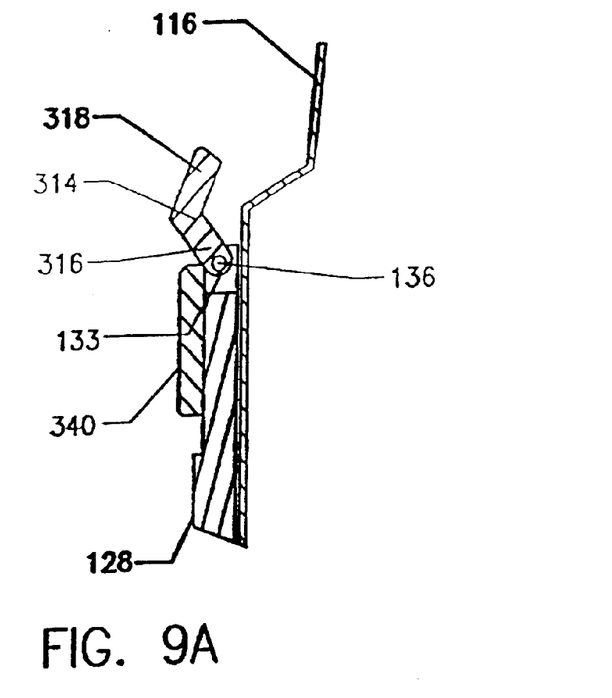
FIG. 9A is an alternate configuration of the locking fingers of the third embodiment of the present invention in an open position.
Figure 9B:
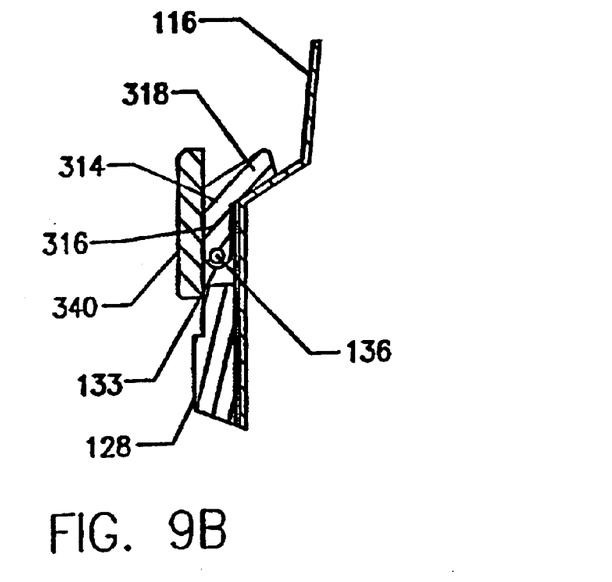
FIG. 9B is an alternate configuration of the locking fingers of FIG. 9A in a closed position.

FIGS. 9A and 9B provide details of an alternative configuration of a locking finger. Specifically, the locking finger 314 of FIGS. 9A and 9B is an angled locking finger formed by an elongated base member 316 and retaining arm 318, preferably integrally formed therewith. Base member 316 is pivotally mounted to cylinder 128 at pivot point 136. The angle between base member 316 and arm 318 is similar to the angle of the taper of front end 120 of the syringe 116 to permit maximum retention of syringe 116 within pressure jacket 112. As shown in FIG. 9A, syringe 116 may be removed from pressure jacket 112 by moving a screw-threaded locking ring 340 toward pressure jacket rear end 132 on threaded surface 134 of cylinder 128. Alternatively, as shown in FIG. 9B, syringe 116 may be held in place by moving the locking ring 340 away from pressure jacket rear end 132 on threaded surface 134 of cylinder 128. As locking fingers 314 are angled, retaining arms 318 serve as stops to prevent the axially outward motion of syringe 116. Thus, locking ring 340 need not include a sloped inner surface, as described above.

Figures 12, 13:
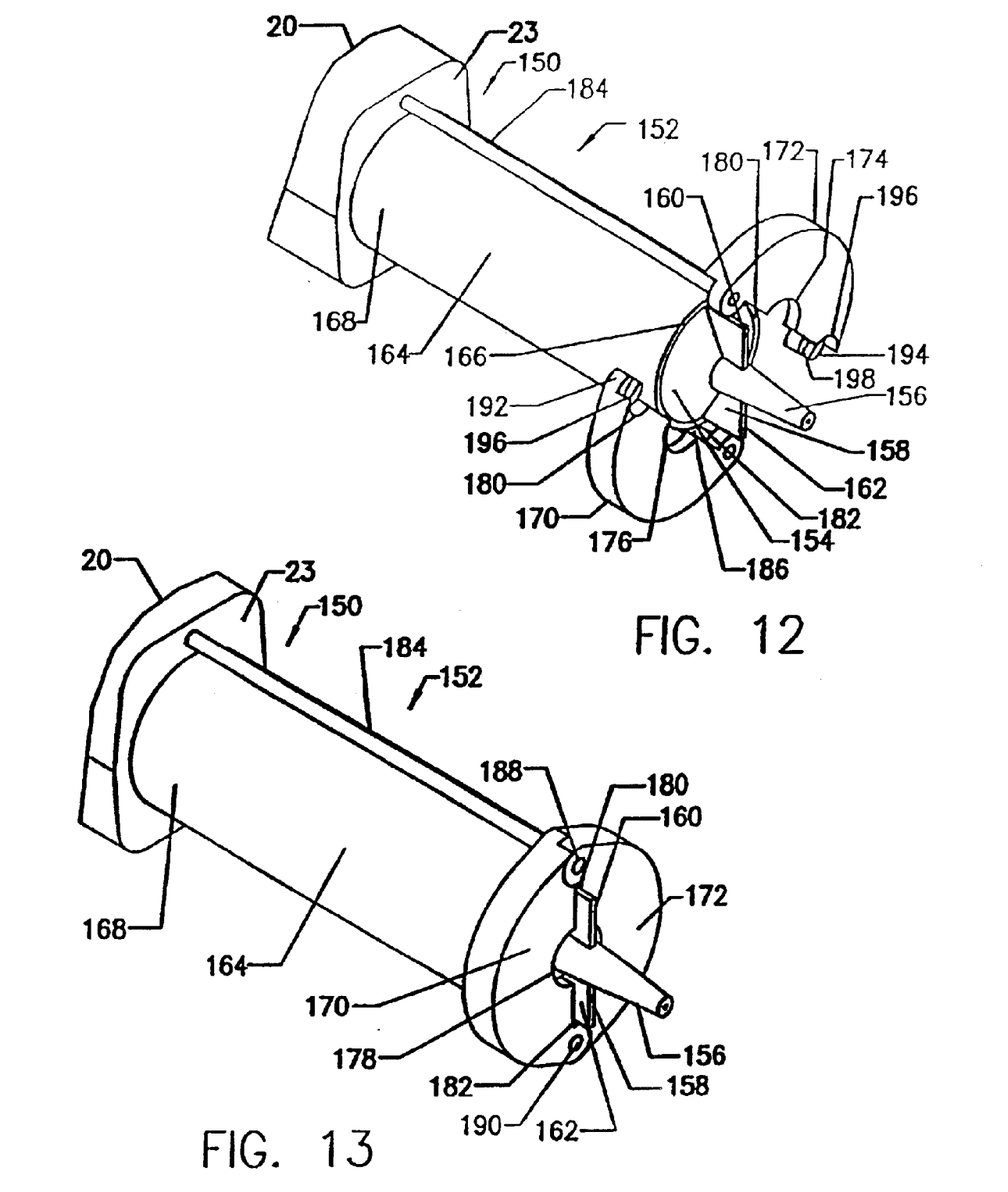
FIG. 12 is a perspective view of a fourth embodiment of the present invention in an open position.
FIG. 13 is a perspective view of the fourth embodiment of the present invention in a closed position.

A fourth embodiment of the present invention is shown in FIGS. 12 and 13. FIG. 12 shows a fluid injection system indicated generally at 150 having a pressure jacket 152 of a split front plate type, in an open position, while FIG. 13 shows the pressure jacket 152 in a closed position. Similar to the third embodiment of the invention, the pressure jacket 152 includes a cylinder portion 164 which may be mounted at its proximal end 168 to the injector front face 23 by any suitable means, such as screw threads (not shown). A cylindrically shaped syringe 154 including a neck 156 may be inserted into the distal end 166 of pressure jacket cylinder 164. Syringe 154 further includes an alignment flange 158 comprising two diametrically opposed radially projecting wings 160 and 162, which aid in the alignment of the syringe 154 with respect to pressure jacket 152. In a preferred embodiment, flange 158 is disposed in a plane including the axis of the syringe 154.

Syringe 154 is held in place by means of a combination of first and second front plates 170 and 172. In a preferred embodiment, first and second front plates 170 and 172 are semi-circular in shape, such that each plate 170 and 172 has one straight margin and one arcuate margin. Plates 170 and 172 each contain semi-circular indentations 174 and 176 in their respective straight margins, and these indentations 174 and 176 form a neck access 178 for the neck 156 of the syringe 154. The straight margins of front plates 170 and 172 act as flange slots 180 and 182, which conform to the wings 160 and 162 of syringe 154. First front plate 170 has an end that is connected to a first tie rod 186, which allows the first front plate 170 to be pivoted between an open position of FIG. 12 and a closed position of FIG. 13. Similarly, the second front plate 172 has an end which is attached to a second tie rod 184, which allows the second front plate 172 to be pivoted between the open and closed positions.

Tie rods 184 and 186 have proximal or rear ends which may simply be rotatably mounted to the injector front face 23, or alternatively attached to gears (not shown) located in injector head 20 for automatic opening and closure. The tie rods 184 and 186 are preferably rigidly attached to the front plates 170 and 172.

When the pressure jacket 152 is in an open position as shown in FIG. 12, front plates 170 and 172 are pivoted away from the pressure jacket 152 by rotating the tie rods 184 and 186. For example, sun and planetary gears (not shown) in the head 20 may provide symmetric rotation of the tie rods 184 and 186. The open position allows the insertion or removal of syringe 154. Once the syringe 154 is inserted within the jacket cylinder 164, the front plates 170 and 172 are pivoted into the closed position as shown in FIG. 13. In this closed position front plates 170 and 172 extend across the front end 166 of jacket cylinder 164. When front plates 170 and 172 are pivoted into the closed position, flange slots 180 and 182 act with the syringe flange wings 160 and 162 of the flange 158 to force the syringe 154 into proper angular alignment within pressure jacket 152. In the illustrated embodiment, in proper alignment the syringe flange 158 is parallel to the plane formed by the tie rods 184 and 186. The flange slots 180 and 182 in conjunction with the syringe flange 158 also act to prevent the syringe 154 from rotating during injector head operation.

FIG. 12 also shows that front plates 170 and 172 include latches 192 and 194, respectively, located at respective ends which are remote from or diametrically opposite from front plate pivot points 188 and 190. Latches 192 and 194 clamp onto the distal ends of tie rods 184 and 186 respectively, and are operable to fix the front plates 170 and 172 in the closed position. Slots 196 and 198 are located near latches 192 and 194, respectively, and are conformable to pivot points 188 and 190, respectively, to permit a snug fit when front plates 170 and 172 are in a closed position. Front plates 170 and 172 may also include conical interior surfaces (not shown) that conform to the front of the syringe 154 when front plates are in a closed position.

The advantages of the first embodiment discussed above are realized with this embodiment. Additionally, the use of flange slots 180 and 182 in conjunction with alignment flange 158 allows automatic alignment of the syringe 154 to an asymmetrical injector head drive means, such as a piston (not shown).

An alternative to the above embodiment may be realized by making the tie rods 184 and 186 integral to the jacket cylinder 164. A second alternative to the above embodiment may be realized by utilizing a syringe similar to that in FIG. 1 and eliminating the flange slots 180 and 182, particularly if there is no need to automatically angularly align the syringe 154.

Figure 14:
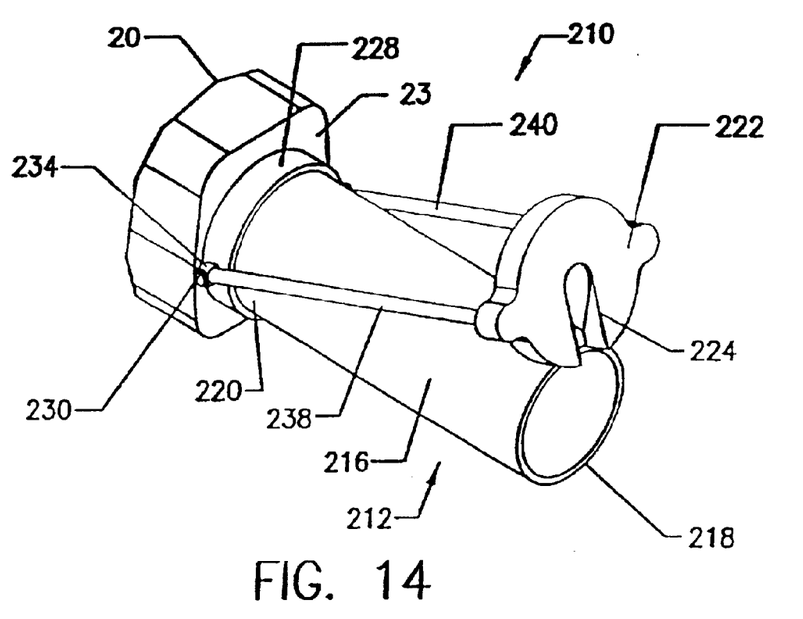
FIG. 14 is a perspective view of a fifth embodiment of the present invention in an open position.
Figure 15:
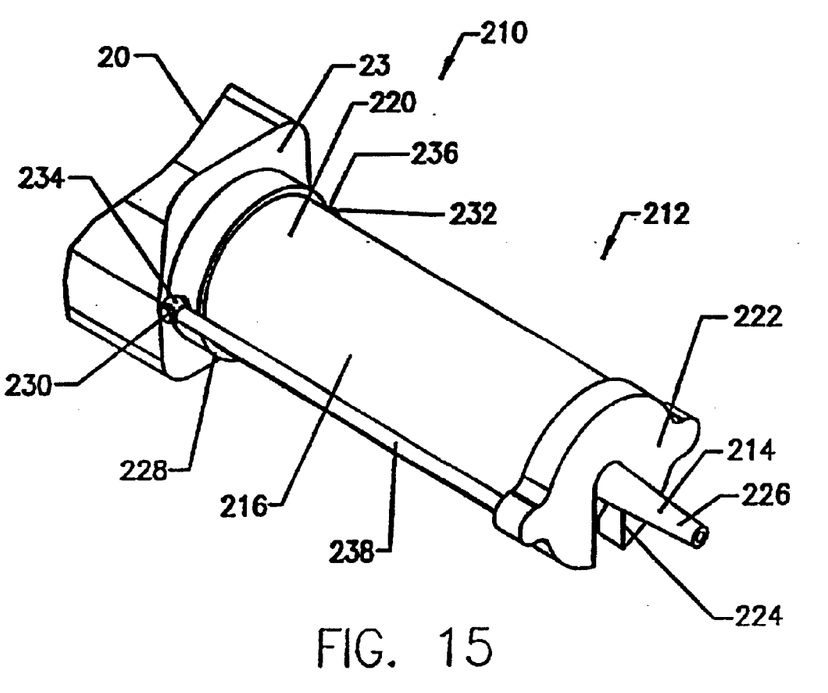
FIG. 15 is a perspective view of the fifth embodiment of the present invention in a closed position.

FIGS. 14 and 15 show a fifth embodiment of the present invention. FIG. 14 shows a fluid injector indicated generally at 210 having a pressure jacket 212 of a swing front retainer type in an open position. FIG. 15 shows the pressure jacket 212 in a closed position. Like the other embodiments previously discussed, the pressure jacket 212 is mounted at its rear end 220 on the injector front face 23 by any suitable means. A syringe 214 inserted into the front end 218 of pressure jacket 212, as shown in FIG. 15, includes a neck 226. The syringe 214 is held in place against force exerted by the injector drive means on the syringe plunger (neither shown) by a front retaining plate 222, which has a slot 224 that allows the neck 226 of the syringe 214 to extend from the cylinder 216 through the front retaining plate 222. The slot 224 is significantly smaller in a direction transverse to the longitudinal axis than the diameter of the syringe 214, so that the remainder of the retaining plate may resist forward-directed force placed on it by the syringe 214 during an injection operation. The slot 224 extends from the center of retaining plate 222 in a direction of the pivot of front plate 222 (discussed below) to the margin of plate 222.

In a preferred embodiment, the inside surface of slot 224 is contoured to engage the outside surface of syringe neck 226. For example, if neck 226 is cylindrical in shape, the inside surface of slot 224 is cylindrical. If neck 226 is conical in shape, the inside surface of slot 224 is angled.

An adapter 228, which is an annular collar for tie rod connections, is mounted or integrally formed on the injector front face 23 and adjoins the pressure jacket cylinder 216. The collar 228 has a pair of tie rod pins 230 and 232. Bushings 234 and 236 rotate about tie rod pins 230 and 232, forming pivots. Bushings 234 and 236 are connected to and may be integrally formed with the rear ends of tie rods 238 and 240. The front ends of tie rods 238 and 240 are connected to the front retaining plate 222. It is understood that pins 230 and 232 may be located either on the injector front face 23 or on the exterior of jacket cylinder 216.

To open the pressure jacket 212, the tie rods 238 and 240, and front retaining plate 222 are pivoted about the pins 230 and 232 by bushings 234 and 236, which allow the syringe 214 to be inserted into the front end 218 of the jacket cylinder 216. The front plate 222 and the rods 238 and 240 are then pivoted back into place to retain syringe 214. It is understood that an alternative to this embodiment may include a front plate 222 formed by two halves each connected to a rod 238 and 240 such that each halve of the front plate 222 is pivoted into place to retain syringe 214. The advantages relating to the first embodiment, as discussed above, are also realized by this embodiment.

Figure 16:
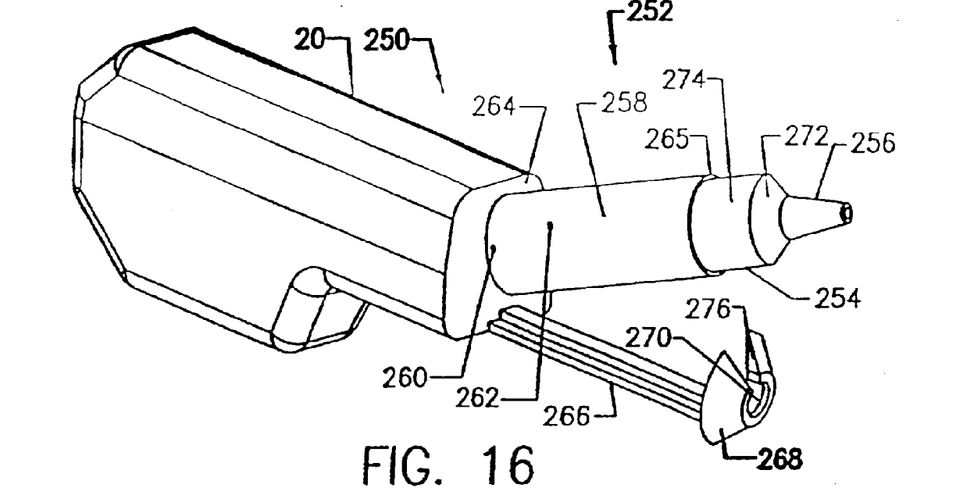
FIG. 16 is a perspective view of a sixth embodiment of the present invention in an open position.

FIG. 16 shows a fluid injector indicated generally at 250 having a pressure jacket 252 of a "caulking gun" type. Like the embodiments already described, the pressure jacket 252, when assembled, permits a piston (not shown) housed within an injector head 20 to apply forward force to a plunger (not shown) within a hollow body of a syringe 254, thereby forcing fluid from a front connector end 256 thereof. The pressure jacket 252 has a jacket cylinder 258 which may be made of clear plastic. The jacket cylinder 258 may be rotated about pins 260 and 262 (the last shown in phantom), which are rotatably attached to the front face 264 of the injector head 20. Front face 264 is curved or slanted which allows cylinder 258 to pivot about pins 260 and 262. Cylinder 258 has an open front end 265 by which the syringe 254 may be loaded or removed.

Figures 17A, 17B:
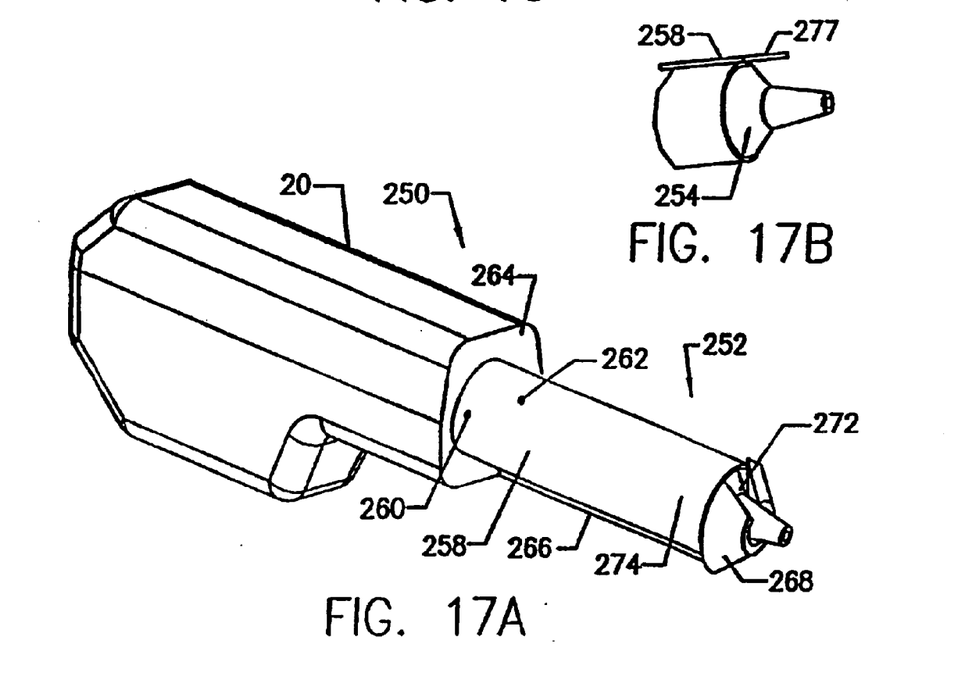
FIG. 17A is a perspective view of the sixth embodiment of the present invention in a closed position.
FIG. 17B is an isolated view of an alternative to the sixth embodiment of the present invention.

Attached to the injector head 20 is the rear end of an elongated arm 266 which is disposed in parallel to the longitudinal axis of syringe 254 when the latter is loaded into pressure jacket 252 and is ready for an injection operation. A retaining wall 268 is orthogonally attached to the front end of arm 266. The retaining wall 268 has an internal surface 270 which is generally spherical or conical in shape so as to mate with an external spherical or conical surface of a syringe transition region 272 located between a syringe cylindrical body 274 and syringe tip 256. Retaining wall 268 has an upwardly open slot 276 for the insertion of the neck 256 of the syringe 254 when the pressure jacket cylinder 258 is moved to a closed position, as shown in FIG. 17A. The slot 276 is cut in the same direction as the direction of articulation of the pivoting pressure jacket 252.

As shown in FIG. 16, cylinder 258 of pressure jacket 252 is pivoted to an open position to allow the loading or removal of the syringe 254 into the open end 265 of the cylinder 258. The cylinder 258 is then pivoted back to rest against the arm 266 and the syringe neck 256 is lowered into the slot 276 of the retaining wall 268. The advantages discussed above are also realized by this embodiment.

FIG. 17B shows an alternative embodiment to that shown in FIG. 17A. A prong 277 attached to cylinder 258 is provided for engaging slot 276 of retaining wall 268 when the pressure jacket 252 is in the closed position so as to further secure syringe 254 within pressure jacket 252.

Figure 18:
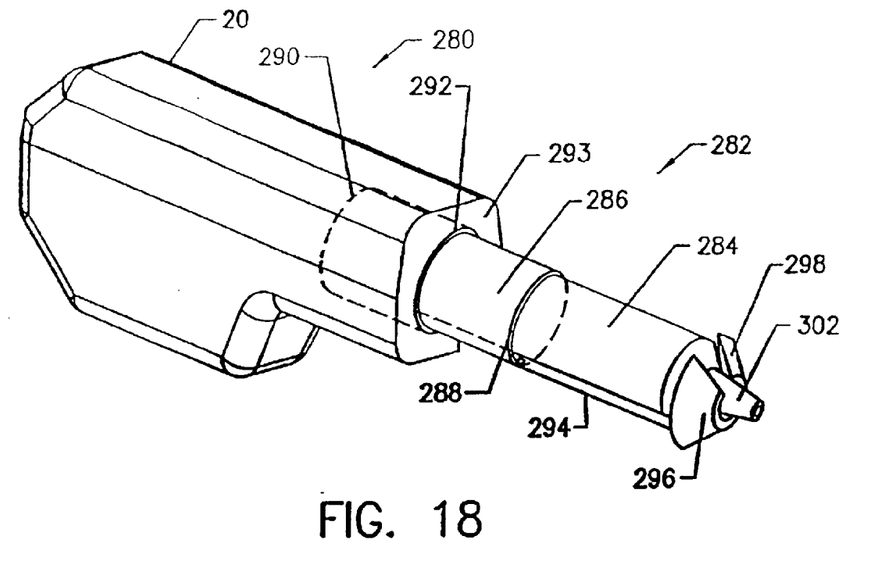
FIG. 18 is a perspective view of a seventh embodiment of the present invention in a partially open position.
Figure 19:
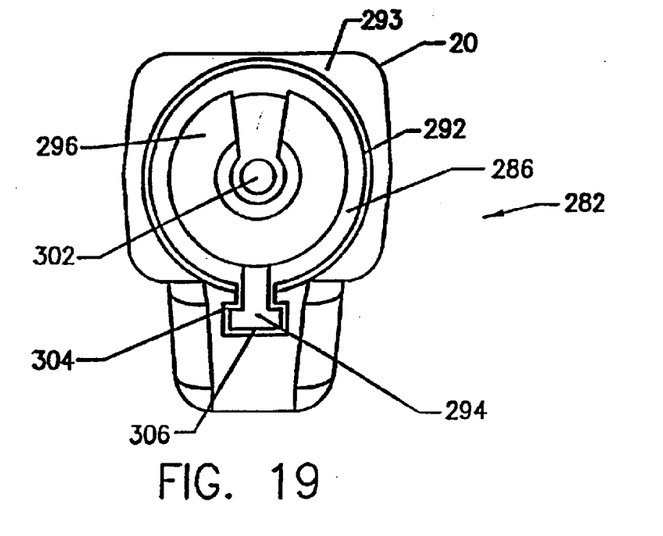
FIG. 19 is a front elevational view of the seventh embodiment of the present invention in a closed position.

FIGS. 18 and 19 show the final embodiment of the present invention which is a fluid injector 280 having a pressure jacket 282 of a "slideable canopy" type for receiving and retaining a syringe 284. The pressure jacket 282 has a canopy 286 that has an open front end 288 and an open rear end 290. Canopy 286 is slidably mounted on the injector head 20. An opening 292 in the front plate 293 of injector head 20 allows the canopy 286 to be retracted within the injector head 20. Canopy 286 is preferably made of clear plastic. Alternatively, canopy 286 may telescope into or over a fixed tube that extends from injector head 20 (not shown).

An arm 294 has a proximal or rear end mounted on the injector head 20. The opposite, distal or front end of the arm 294 is orthogonally attached to a retaining wall 296 which has a slot 298 to allow placement of the neck 302 of the syringe 284. In operation, the syringe 284 is placed on the arm 294 such that the neck 302 of syringe 284 is placed within the slot 298 of the retaining wall 296. The retaining wall 296 has a conical shape to conform to the front of the syringe 284. In order to hold the syringe 284 in place, the canopy 286 is moved along the arm 294 as by means of a channel 304, as shown in FIG. 19, formed in the interior surface 306 of the canopy 286. This arrangement allows the canopy 286 to slide on the arm 294 from an open to a closed position or vice versa, allowing the removal or insertion of syringe 284. The advantages discussed above are also realized by this embodiment.

The above-described embodiments are merely illustrative of the principles of this invention. Other arrangements and advantages may be devised by those skilled in the art without departing from the invention. The scope of the invention is indicated by the following claims, rather than by the foregoing description. All changes or modifications that fall within the meaning and range of equivalency of the claims are to be embraced within their scope.

What is claimed is:

1. A fluid injection apparatus for use with a syringe, the fluid injection apparatus comprising:

an injector comprising a housing defining a front opening therein and a drive piston extendable through the front opening of the housing for imparting motive force to a plunger disposed within the syringe; and a pressure jacket assembly operably associated with the housing for substantially enclosing the syringe during an injection procedure, the pressure jacket assembly comprising:

a jacket cylinder comprising a rear end coupled to the injector housing and an open front end for receiving the syringe therethrough;

at least one support member comprising a rear end pivotally coupled to the injector housing and a front end; and a front member pivotally coupled to the front end of the at least one support member, wherein the front member is pivotable between a closed position for retaining the syringe within the jacket cylinder and an open position for allowing the syringe to he inserted into and removed from the front end of the jacket cylinder.

2. The fluid injection apparatus of claim 1 wherein the front member is adapted to engage a front wall of the syringe to retain the syringe within the jacket cylinder.

3. The fluid injection apparatus of claim 1, further comprising a second support member having a rear end and a front end, the rear end of the second support member being pivotally connected to the injector housing.

4. The fluid injection apparatus of claim 3 wherein the front end of the second support member is pivotally connected to the front member.

5. The fluid injection apparatus of claim 3, further comprising a second front member connected to the front end of the second support member, wherein the second front member is pivotable between a closed position for retaining the syringe within the jacket cylinder and an open position for allowing the syringe to be inserted into and removed from the jacket cylinder.

6. The fluid injection apparatus of claim 5 wherein the front member and the second front member cooperate to retain the syringe within the jacket cylinder.

7. The fluid injection apparatus of claim 1 wherein the front member defines a slot for receiving a neck of the syringe.

8. The fluid injection apparatus of claim 1 wherein the at least one support member comprises a tie rod.

9. The fluid injection apparatus of claim 4 wherein the front member defines a slot for receiving a neck of the syringe.

* * * * *